United States Patent
Ragazzini et al.

Patent Number: 5,351,525
Date of Patent: Oct. 4, 1994

[54] PROCESS FOR GENERATING, BY WAY OF EXPERIMENTAL TESTS, THE CAPILLARY PRESSURE CURVE IN A POROUS MEDIUM

[75] Inventors: Giovanna Ragazzini, Milan; Carlo Venturini, Castiglione D'Adda, both of Italy

[73] Assignee: AGIP S.p.A., Milan, Italy

[21] Appl. No.: 106,642

[22] Filed: Aug. 16, 1993

[30] Foreign Application Priority Data

Aug. 27, 1992 [IT] Italy .................. MI92 A 002019

[51] Int. Cl.⁵ ........................................... G01N 15/08
[52] U.S. Cl. ........................................ 73/38; 73/153
[58] Field of Search .................. 73/153, 38; 422/72, 422/270; 494/10, 901, 42

[56] References Cited

U.S. PATENT DOCUMENTS 4,868,751  9/1989  Dogru ............................... 73/38

FOREIGN PATENT DOCUMENTS 0106398  4/1984  European Pat. Off. .
0206372  12/1986  European Pat. Off. .

OTHER PUBLICATIONS

Transactions of the Aime, vol. 160, pp. 114–123, G. L. Hassler, et al., "Measurement of Capillary Pressures in Small Core Samples".
Soviet Inventions Illustrated, Section Ch, Week 9126, Aug. 14, 1991, "Unit for Determinin. of Coefft. of . . . ".

*Primary Examiner*—Hezron E. Williams
*Assistant Examiner*—Michael Brock
*Attorney, Agent, or Firm*—Oblon, Spivak, McClelland, Maier & Neustadt

[57] ABSTRACT

A technique is disclosed for obtaining the true capillary pressure curve directly from experimental measurements. The above said technique is based on the use of a small-size sample being into capillary contact with the sample to be tested, with the usual tail effects being thus prevented. The resulting experimental data does not require complex mathematical processing yielding approximate results.

7 Claims, 5 Drawing Sheets

PROCESS FOR GENERATING, BY WAY OF EXPERIMENTAL TESTS, THE CAPILLARY PRESSURE CURVE IN A POROUS MEDIUM

The present invention relates to a process for generating, by means of experimental measurements, the capillary pressure curve in a porous medium.

The capillary pressure curve is a relationship between the saturation of fluids contained inside the porous medium, and the corresponding capillary pressure (i.e., the pressure drop between said fluids).

Said curve is used by the industry, in particular by petroleum industry, in order to learn the distribution of the various fluids inside the porous media.

In fact, in reservoir rocks, the capillary forces, by not allowing a sharp separation between the involved fluids (water, oil and/or gas), are responsible for the existance of a "transition zone" characterized by the co-presence of the fluids in different percentages.

Inasmuch as the capillary pressure varies as a function of the level, calculated from that zone in which only the heaviest fluid, i.e., water, is present, the capillary pressure curve also expresses the—always decreasing—relationship between water saturation and the height above free water level.

Knowing the distribution in height of the fluids in a reservoir results hence to be essential in order to determine which are the well zone to be perforated in order to produce oil or gas, and those to be sealed in order to prevent water production.

Among the laboratory techniques which are commonly used in order to determine the capillary pressure curve, the most widely diffused technique is the one based on the use of a centrifuge. This is a fast procedure which consists in submitting the porous medium, of cylindrical shape, saturated with a fluid ($F_1$) and immersed in another fluid ($F_2$) immiscible with the first fluid, to centrifugation.

During the centrifugation, the fluid $F_2$ succeeds in penetrating the porous sample, displacing the fluid $F_1$.

When the equilibrium of fluids is reached for each speed at which the centrifuge rotor is caused to revolve, the value of saturation of $F_1$ inside the sample is measured.

These experimental tests cause problems of data interpretation, because the saturation of $F_1$ which is measured actually is an average value throughout the sample.

In fact, for a sample which revolves in the centrifuge at a certain given revolution speed, the saturation of fluid $F_1$ is not constant, but varies along the axis of the sample. This is caused by the presence of a pressure gradient, caused by the artificial gravitational field resulting from the revolution, which varies as a function of the distance from centrifuge rotor.

FIG. 1 shows the behaviour of capillary pressure as a function of certain measuring revolution speeds, along a 5 cm-long sample submitted to centrifugation, in case of air-water displacement. The trend can be obtained by the equation (I)

$$P_c(r) = 0.5 \Delta \rho w^2 (R_2^2 - r^2) \quad (I)$$

wherein r ($R_1 < r < R_2$) is the distance from the revolution axis, of a point of the cylindrical sample which is being tested, $P_c(r)$ is the capillary pressure at distance r, $R_1$ and $R_2$ represent, respectively, the outer and inner sample radiuses, w is the revolution speed, $\Delta \rho$ is the difference between density values of the two fluids.

Consequently, the capillary pressure varies from 0 at $r = R_2$, and reaches its maximal value at $r = R_1$ for each measuring revolution speed.

The most widely used procedures in order to obtain the capillary pressure curve from centrifugation tests consist in analysing the experimental values through several mathematical relationships.

The average saturation as a function of distance is supplied by equation (II)

$$\overline{S}(P_{c1}) = \frac{1+R}{2P_{c1}} \int_0^{P_{c1}} \frac{S(P_c) dP_c}{\sqrt{1 - \frac{P_c}{P_{c1}}(1 - R^2)}} \quad (II)$$

in which $S(P_c)$ indicates the Local capillary pressure curve, $\overline{S}(P_{c1})$ is the average saturation rate calculated at that sample end which is the nearest to the revolution axis, R is equal to $R_1/R_2$.

The problem consists reversing this first-species Volterra integral, so as to be able to obtain the local curve $S(P_c)$ from the experimental data $\overline{S}(P_{c1})$.

Several solutions for this equation were proposed, which resorted both to a differentiation of the experimental data, and to a differentiation and integration thereof.

So, Hassler G. L. and Brunner E. (Trans. AIME, 1945, Vol. 160, pages 114–123), by negliging the centrifuge gravity gradient, obtained a solution which is only valid in the case of small size samples ($R_1/R_2 > 0.7$). This solution suffers from the drawback that the saturation values are underestimated, and the involved error is only small for low saturation rates.

Hoffman R. N. (SPEJ, 1963, vol. 3, pages 227–235) and van Domselaar H. R. (Rev. Tec. Intevep., 1984, Vol. 4, n°1, pages 55–62) obtained approximate solutions of equation (II). In particular, the solution proposed by van Domselaar systematically overestimates the saturation values and is accurate in high-saturation range for longer samples. These solutions furthermore show the considerable drawback that they are influenced to a considerable extent by the experimental errors.

Rajah R. R. (SPWLA J, 1986, pages 1–18), with the aid of a hypothesis as to the slope of average saturation rate, obtained the solution represented by equation (III), which is valid within the range of $0.5 < R_1/R_2 < 1$.

$$S(P_{c1}) = \overline{S}(P_{c1}) + \frac{2R}{1+R} P_{c1} \frac{d\overline{S}(P_{c1})}{dP_{c1}} + \quad (III)$$

$$\frac{R}{(1-R^2)} \int_0^{P_{c1}} \left[ \frac{1}{\left(1 - \frac{P_c}{P_{c1}}(1-R^2)\right)^{\frac{1}{2}}} - 1 \right]^2 \frac{d\overline{S}(P_c)}{dP_c} dP_c$$

The solution proposed by Rajan is more accurate than the preceding ones, and can be regarded as the best approximation presently available. Owing to the presence of derivatives and of an integral, however, this approximation requires the use of a function in order to fit the experimental saturation data relatively to capillary pressure.

Forbes P. (SCA Conference Paper No. 9107, 1991) obtained an accurate, but anyway still approximate, solution (IV) of equation (II)

$$S_{i-\frac{1}{2}+B/4}=(1-B)S_{\alpha i-\frac{1}{2}}+B/2S_{\beta i} \tag{IV}$$

wherein:

$$S_{\alpha i-\frac{1}{2}} = \frac{\overline{S}_i - (P_{i-1}/P_i)^{1+\alpha}\overline{S}_{i-1}}{1 - (P_{i-1}/P_i)^{1+\alpha}}$$

$$S_{\beta i} = (P_{i-1}/P_i)^{1+\alpha}S_{\beta i-1} + \frac{1 - (P_{i-1}/P_i)^{1+\beta}}{1 - P_{i-1}/P_i} \overline{S}_i - \frac{P_{i-1}}{P_i}\overline{S}_{i-1}$$

$$B = 1 - R^2, 0 \leq B \leq 1, \alpha = \frac{R_2 - R_1}{R_2 + R_1}, \beta = 2/\alpha$$

$i-\mu(0 \leq \mu \leq 1)$ is the value of the function at pressure $$P_i - \mu[P_iP_{i-1}],$$

with the constraint $S_{j+1}<S_j$, which prevents possible oscillations of the results.

All of these solutions suffer of the drawback that they require more or less fine approximations, and the use of more or less sophisticated mathematical processing.

A process has been found now according to the present invention, which makes it possible the true capillary pressure curve inside a porous medium to be directly determined by way of experimental tests, without the aid of mathematical processing.

In accordance therewith, the present invention relates to a process for generating the capillary pressure curve of two immiscible, non-reactive liquids inside a porous medium by means of the technique of centrifugation of cylindrical samples at various revolution speeds, which process comprises:

(1) centrifuging an assembly, saturated with a first fluid, constituted by the porous sample to be analysed (A), and a material (B) having the same permeability and approximately the same diameter as of (A), the material (B) being connected with the sample (A) through capillary contact along that section of (A) which is the farthest from centrifuge rotor, with the ratio of the length of (A) to the length of (B) being comprised within the range of from 10:1 to 2:1, preferably of from 7:1 to 4:1, with the assembly constituted by (A) and (B) being immersed in a second fluid which is immiscible with the first fluid;

(2) measuring the saturation rate of the first fluid by weighing the only sample (A);

(3) correlating, for each measuring revolution speed, the so determined saturation rate value, with the corresponding average capillary pressure of (A)+(B) assembly.

By the term "non reactive", fluids are meant which are devoid of chemical reactivity both with each other, and with materials (A) or (B).

Figure 1:
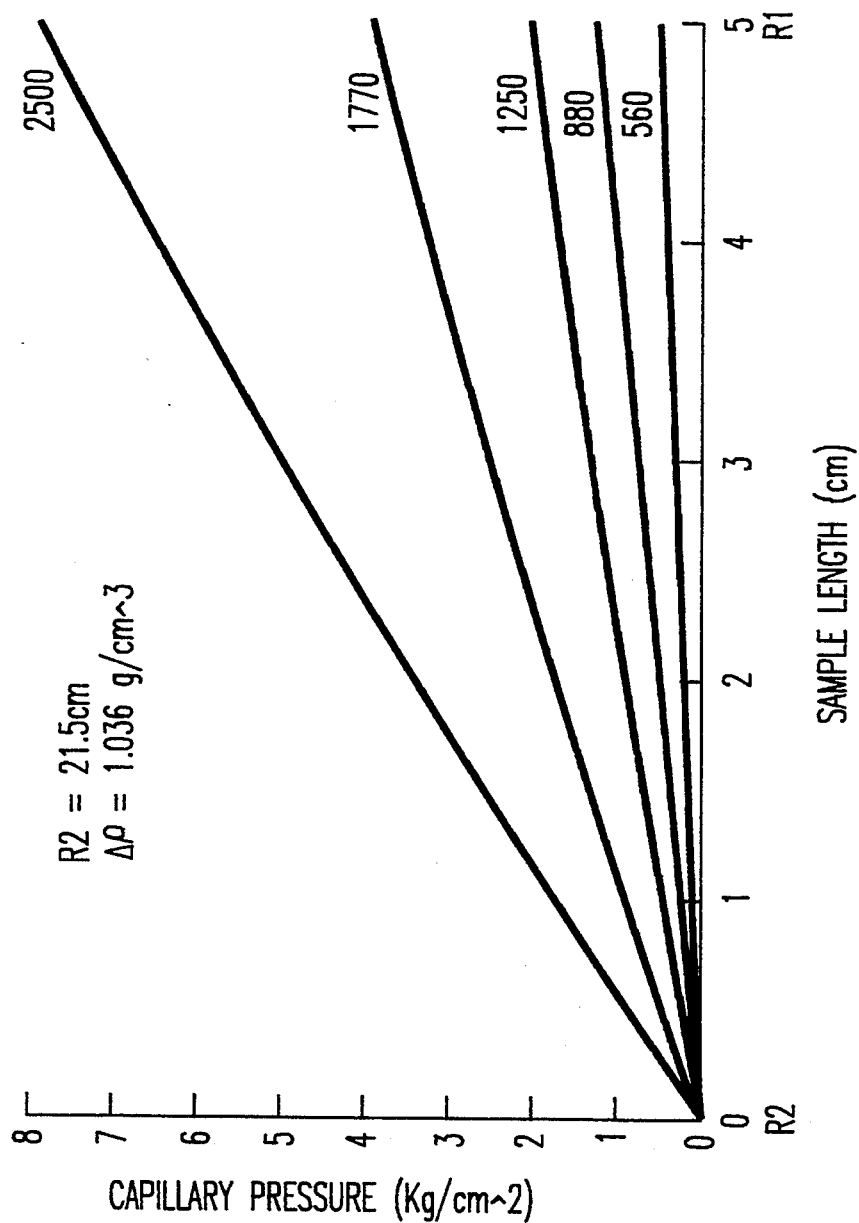
FIG. 1 illustrates the behavior of capillary pressure along a 5 cm long sample submitted to centrifugation.
Figure 2:
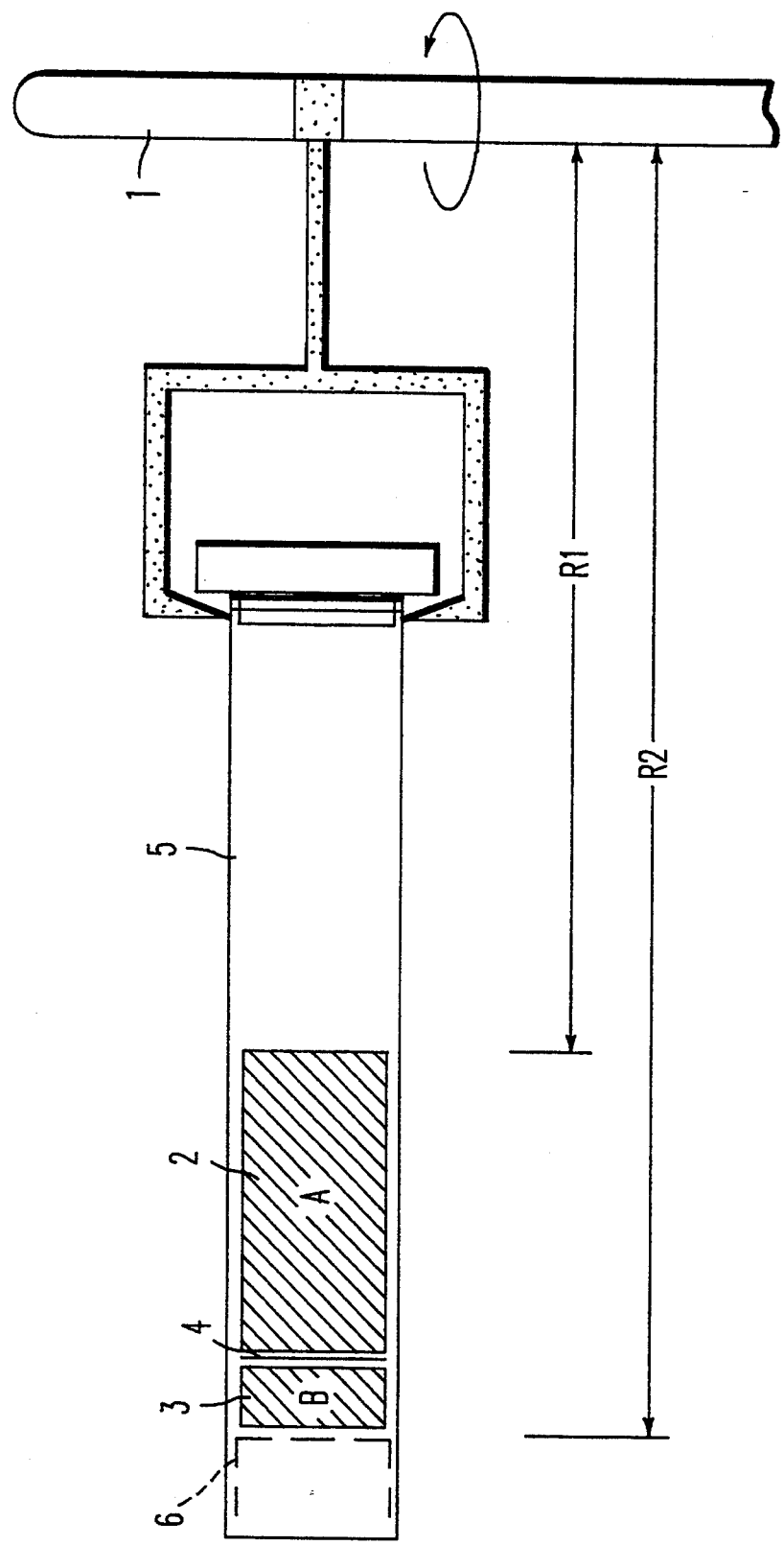
FIG. 2 is a schematic of a centrifuge apparatus.

In FIG. 2, which illustrates the present invention, (1) is the centrifuge rotor, (2) is the sample to be analysed (A), (3) is the material (B) put into capillary contact (4) with the sample (A), (5) is the sample carrier used, (6) is a perforated basis on which (B) rests, which is used in order to prevent the soaking of the displaced fluid during centrifuge deceleration.

For the studies of capillary pressure in the field of petroleum industry, both the sample (A) and the material (B) are rock samples having the same lithological, permeability and porosity characteristics.

According to a preferred embodiment, the material (B) comes from the same portion of the well core as of (A).

By using the normal commercial centrifuges and the usual sample carriers, the cylindrical samples of (A) have a length of from 1 to 12 cm, preferably of from 2 to 7 cm.

The (A) and (B) components of the assembly, the ratio of the respective lengths of which is comprised within the range of from 10:1 to 2:1, preferably of from 7:1 to 4:1, are put into capillary contact by means of a thin layer of cellulose soaked with the same fluid which initially saturated the sample ($F_1$).

As an alternative, the capillary contact may be accomplished by means of the simple (A)/(B) contact.

At each revolution speed of the centrifuge, once that the equilibrium of fluids is reached (after a time estimated to be, by excess, of approximately 8 hours), the value of saturation is determined by only weighing the sample to be analysed (A).

The sample (A) is removed from the sample carrier, with the latter being kept in the vertical position, and the saturation of fluid $F_1$ is determined by weighing operations by means of the equation (V):

$$S_{F1i}=100-S_{F2i} \tag{V}$$

wherein $$S_{F2i} = \frac{100}{1 - \frac{\rho F_2}{\rho F_1}} \cdot \frac{P_s - P_i}{P_1}$$

In these equations, $S_{F1i}$ and $S_{F2i}$ respectively are the saturation rate of fluids $F_1$ and $F_2$ at the i-th revolution speed, $P_i$ is the weight of the sample at the i-th revolution speed, $P_s$ is the weight of the sample (A) under saturation conditions and $P_1$ is the weight of $F_1$ when sample (A) is completely saturated.

By way of experimental tests, the present Applicant was able to observe that the above said samples are meaningfully lower, in particular at lower capillary pressure values, than as obtainable by only centrifuging the sample (A) without the body (B).

The capillary pressure curve obtained by reporting, for each revolution speed, the corresponding average saturation rate of (A), computed as reported above, on a chart, vs. the average capillary pressure of the whole system constituted by the sample (A) plus the sample (B).

Such an average capillary pressure ($\overline{P}_c$) can be calculated for each revolution speed by means of the following equation (VI):

$$P_c = 0.25\Delta\rho w^2 (R_2{}^2 - R_1{}^2) \quad \text{(VI)}$$

wherein $w = \pi N/30$, wherein N is the revolution speed (revolution per minute) of the centrifuge.

The method according to the present invention, which simulates the displacement which takes place in a longer sample (A)+(B) and takes into account only the saturation values of (A), makes it possible the saturation rate values not to be measured in that portion of assembly sample (A)+(B) in which the tail effects take place, and higher values of capillary pressure to be reached with the centrifuge revolution speed being the same. Thus, in the sample (A), a less variable saturation behaviour will be reached, with said saturation rate becoming a constant at high revolution speeds.

The process according to the present invention, disclosed herein above by operating at a temperature of 21° C., can also be applied to a wider temperature range, preferably of from 10° to 80° C., with the maximal temperature being a function of the boiling point of the fluid.

Therefore, as compared to the prior art, the process of the present invention does not require any, more or less approximate, mathematical processing.

It derives from the above, as an obvious advantage, that these measurements can be carried out with a high reliability degree also with no software aids.

Furthermore, the capillary pressure curves obtained by means of the process disclosed hereinabove are not subject to the approximations of the interpolations and solutions of equation (II).

The technique disclosed hereinabove, which was proven to be valid on rock samples using water-air and water-oil fluids, can be also applied to other types of porous materials and other pairs of immiscible fluids, provided that they do not react with the porous medium being tested.

The following examples are reported for a better understanding of the present invention.

EXAMPLES

Equipment

A refrigerated centrifuge Beckman J6M, modified in order to make it possible the international rotor 287 for tests for petroleum industry to be used, which makes it possible 4 sample carriers to be centrifuged simultaneously, is used (at various revolution speeds, up to a maximal revolution speed of 3500 rpm).

A 16.5 cm long cylindrical sample carrier of aluminum having a diameter of 3 cm is used. The bottom portion of said sample carrier supports a perforated separator, which prevents the displaced fluid from being absorbed again by the sample during centrifuge deceleration.

The capillary contact between the samples and the material arranged at sample end is secured by the use of a thin paper disk saturated with salty water.

In order to determine the saturation by weighing, an analytical balance (Mettler PE160) is used, which has a sensibility of one thousandth of a gram.

Samples preparation

The samples to be tested, sandstones drawn from an outcrop, as well as from a petroleum well, have a size of approximately 5 cm of length and 2.7 cm of diameter. They were so selected as to cover a wide permeability range, of from 30 to 760 mD.

The samples are submitted to the customary extractions with a Soxhlet extractor, alternatively using chloroform and water/methanol mixtures, and are dried in an oven at approximately 100° C.

The permeability is determined by using nitrogen under three different pressure values, and applying the Klinkenberg's correction. The porosity is measured by means of the method based on resaturation with water.

The petrophysical characteristics of the samples are reported in Table 1, in which L is the length of the sample, D is the diameter of its base, K is the permeability expressed as millidarcy, 0 is the porosity as referred to total sample volume.

TABLE 1

| Sample (No.) | L (cm) | D (cm) | K (mD) | 0 (%) |
|---|---|---|---|---|
| 1 | 4.9 | 2.7 | 192 | 18.6 |
| 2 | 4.9 | 2.7 | 757 | 21.3 |
| 3 | 4.9 | 2.7 | 31.7 | 16.8 |
| 4 | 4.9 | 2.7 | 85.8 | 15.0 |

Measurements of air-salty water displacement

To the sample carrier of the centrifuge, "assembly samples" are charged, which are constituted by:

A) an inner sample of about 5 cm;

B) an external sample of approximately 1 cm, put into capillary contact with the first, inner sample, by means of a paper disk.

The "assembly" samples prepared in that way are submitted to centrifugation. The average values of saturation rate with salty water are determined by weighing each sample (A) after eight hours of revolutionary motion at a preset value of revolution speed (measurement revolutions per minute). The equation (V) is applied, with the weights being expressed as grammes.

We were able to verify that the deceleration of the centrifuge and its being stopped for the necessary time for carrying out the measurement (20 minutes for four samples) do not affect in any way the equilibrium of the fluids. and consequently their saturation rates.

On the contrary, as the "global capillary pressure", the average pressure value of the assembly sample (A)+(B) is considered. Such a value is obtained, as $kg/cm^2$, from equation (VI), with $R_1$ and $R_2$ being expressed as cm, w as radians/second, N being expressed as rpm, $\rho$ as $g/cm^3$, and by multiplying times the factor $k = 1.1417 * 10^{31\ 6}$ for the conversion of measurement units.

Water used in the measurements shows a salinity (as NaCl) of 50,000 ppm, a specific gravity of 1.036 $g/cm^3$; temperature is 21° C. The results are reported in following Table 1.

TABLE 1

| RPM | Average $P_c$ | Water saturation rate (%) | | | |
|---|---|---|---|---|---|
| | | Sample 1 | Sample 2 | Sample 3 | Sample 4 |
| 330 | 0.075 | 94.2 | 66.4 | — | — |
| 400 | 0.11 | 82.1 | 48.3 | 96.3 | 89.5 |
| 560 | 0.22 | 54.9 | 35.0 | 80.8 | 65.6 |
| 880 | 0.55 | 33.5 | 22.7 | 49.5 | 38.1 |
| 1250 | 1.11 | 25.1 | 17.8 | 36.0 | 31.6 |
| 1770 | 2.22 | 19.7 | 14.3 | 27.8 | 24.4 |
| 2500 | 4.43 | 15.7 | 11.5 | 19.7 | 19.1 |
| 3500 | 8.69 | 11.6 | 8.7 | 14.9 | 14.7 |

Figure 3B:
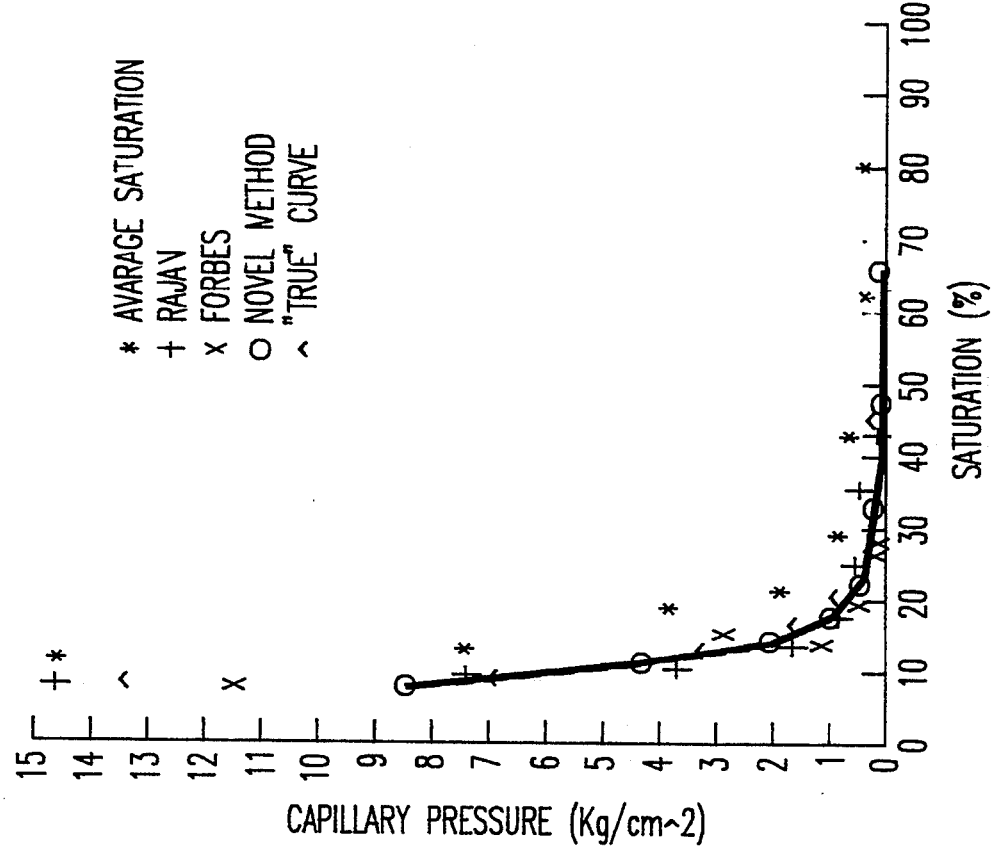
FIG. 3 illustrates the measurement of air-salty water displacement for Samples 1 and 2.
Figure 3A:
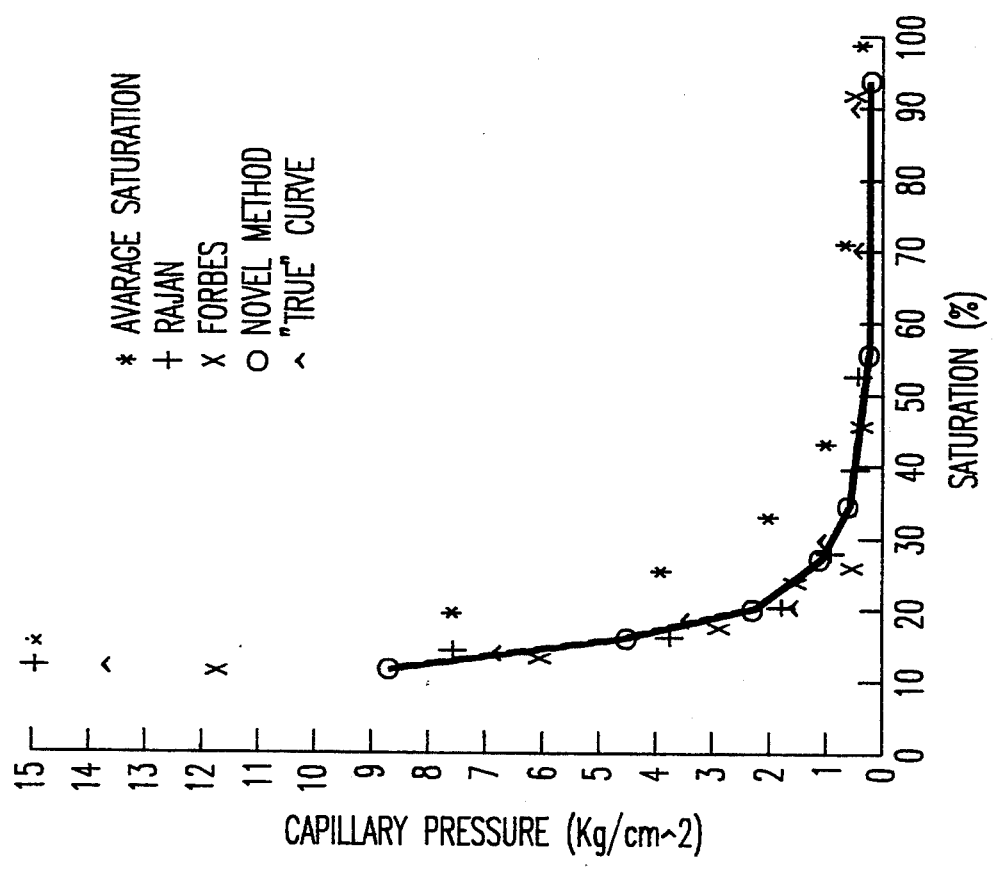
Figure 4B:
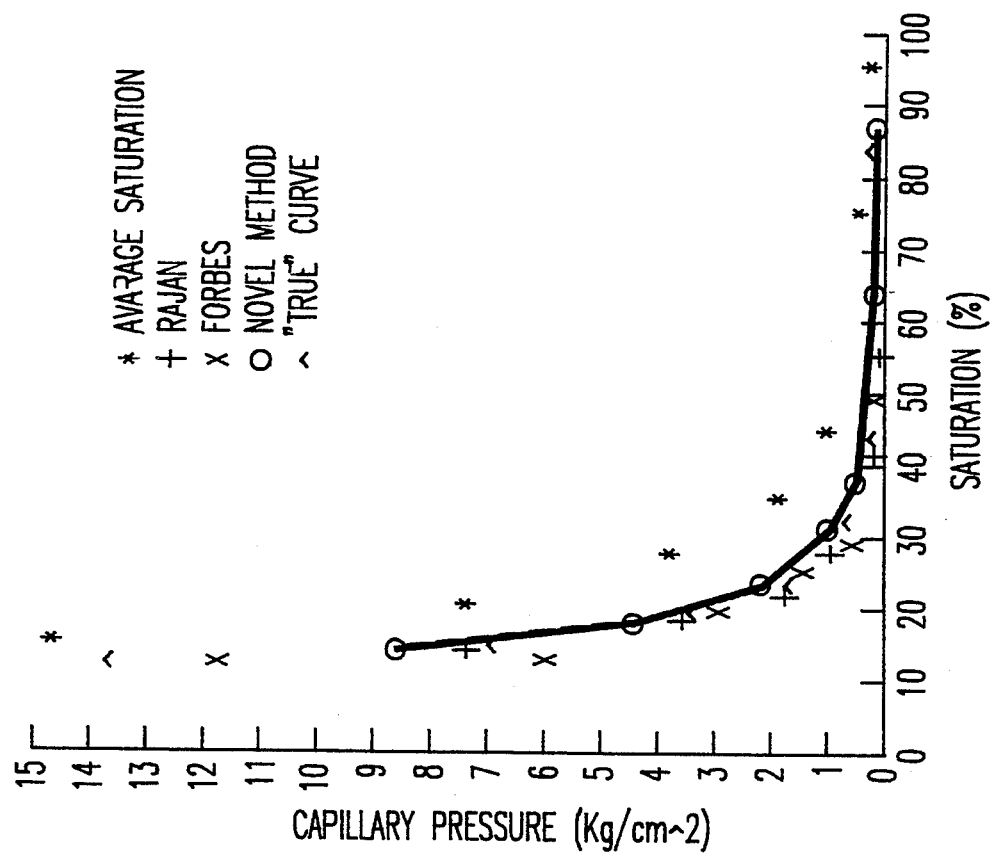
FIG. 4 illustrates the measurement of air-salty water displacement for Samples 3 and 4.
Figure 4A:
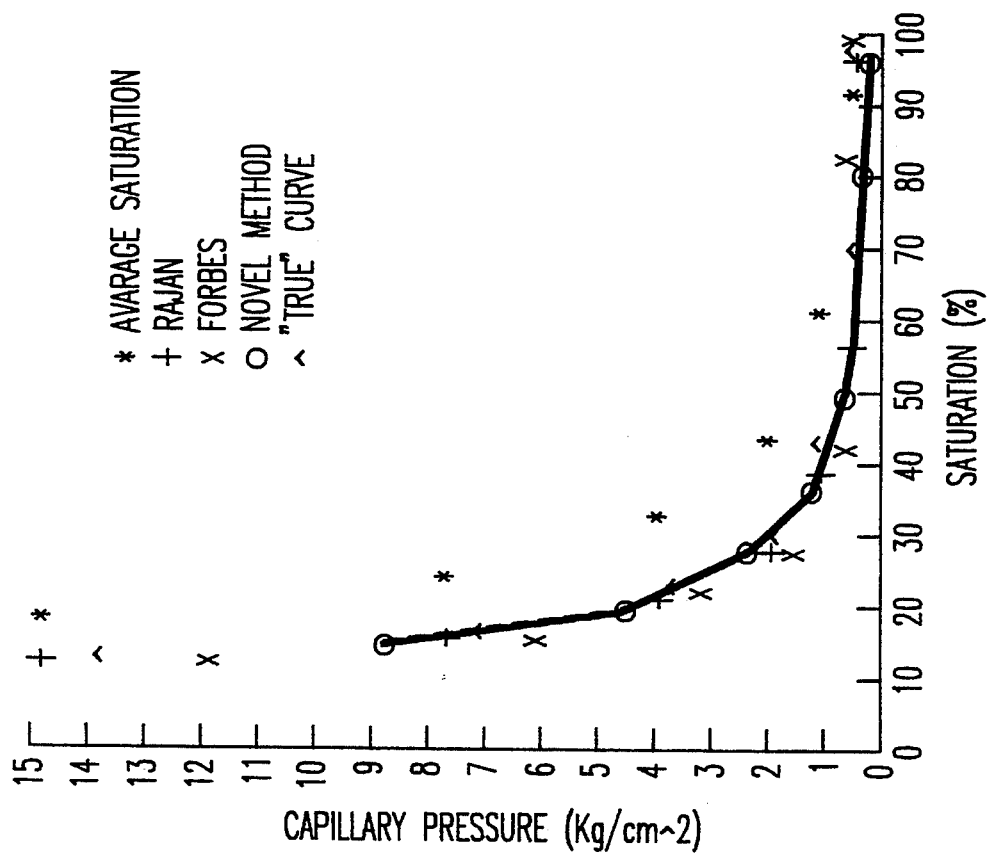

The experimental data obtained in that way are reported in chart form in FIGS. 3 and 4, in which, for comparison purposes, also the raw experimental value are reported which can be obtained according the customary experimental techniques (that is to say, by submitting to centrifugation only the several "A" samples), together with the values resulting from the mathematical processing according to the solutions proposed by Rajan and Forbes.

In said Figures, also the "true" $P_c$ is reported, which is obtained by means of destructive tests from the average saturation rate of a thin slice of sample, characterized by a well defined value of capillary pressure.

It can be observed that the data obtainable according to the method of the present invention are:
i) very much different from the experimental values as measured according to the technique known from the prior art;
ii) matching in a nearly perfect way, the "true" capillary pressure curve;
iii) matching those obtainable from the solutions according to Rajan and Forbes [equations (III) and (IV)].

Measurements of oil-salty water displacement

The samples 1 and 2 disclosed hereinabove are submitted to measurements of oil-salty water displacement [i.e., by saturating (A) and (B) with salty water and then centrifuging them in oil]according to the same procedure as disclosed for air-salty water displacement, caring of removing the excess of oil present on sample (A) before carrying out the weighing operation.

A synthetic oil was used, which is constituted by isoparaffinic hydrocarbons (specific gravity=0.756 g/cm$^3$), available under the trade name Soltrol 130 (registered trade mark of Company Phillips 66).

The results of these experimental tests are reported in Table 2.

TABLE 2

| RPM | Average $P_c$ | Water saturation rate (%) Sample 1 | Sample 2 |
|---|---|---|---|
| 530 | 0.054 | 93.7 | 66.1 |
| 630 | 0.075 | 78.7 | 48.7 |
| 760 | 0.11 | 65.7 | 39.5 |
| 1070 | 0.22 | 41.9 | 24.6 |
| 1690 | 0.50 | 27.7 | 17.5 |
| 2400 | 1.11 | 23.2 | 13.5 |
| 3500 | 2.36 | 18.0 | 11.5 |

Figure 5B:
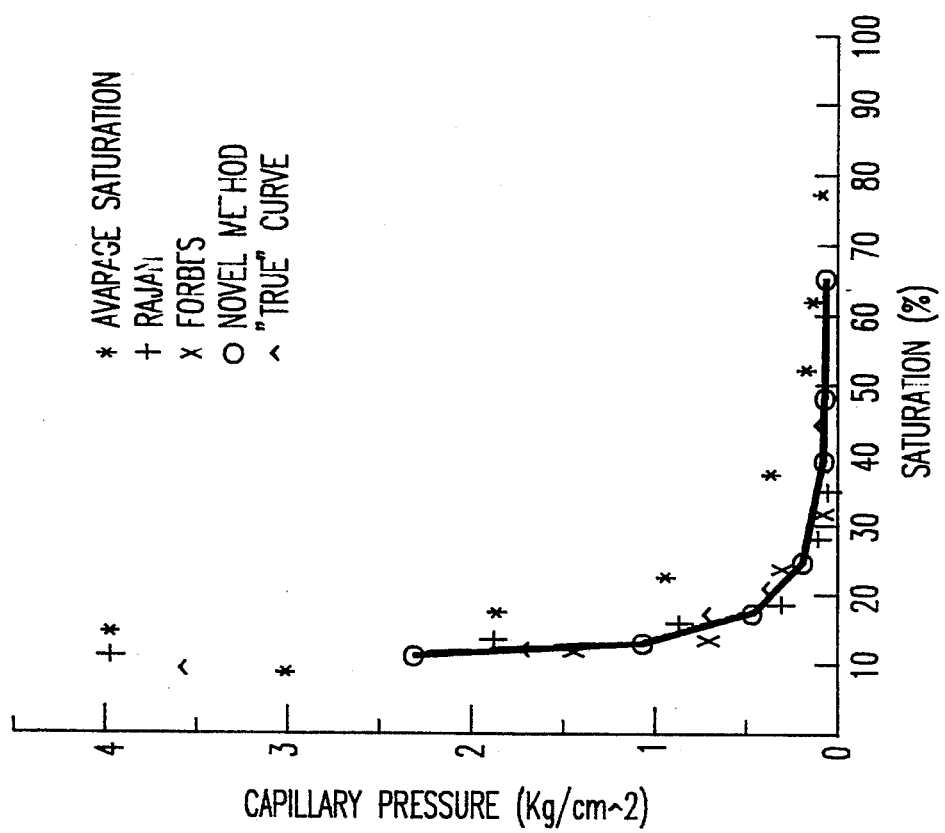
FIG. 5 illustrates the measurement of oil-salty water displacement for Samples 1 and 2.
Figure 5A:
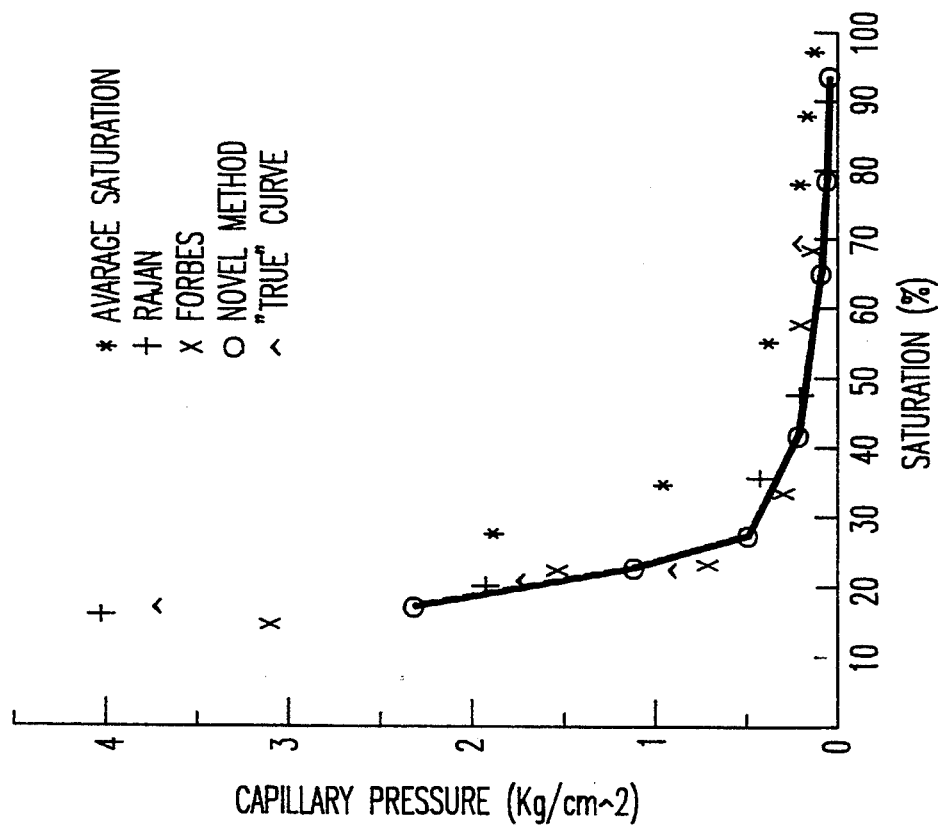

The resulting experimental data are reported in chart form in FIG. 5, on which for comparison purposes also the raw experimental values are reported, which can be obtained according to the usual techniques, i.e., by centrifuging only the several samples (A); as well as the processed values according to the solutions proposed by Rajan and Forbes, and the "true" capillary pressure curve obtained by means of destructive tests.

Also in this case, one may observe that the data according to the present invention are:

i) very much different from the experimental values as measured according to the technique known from the prior art;
ii) matching in a nearly perfect way, the "true" capillary pressure curve;
iii) matching those obtainable from the solution according to Rajan and Forbes [equations (III) and (IV)].

We claim:
1. Process for generating the capillary pressure curve of two immiscible, non-reactive liquids inside a porous medium by means of the technique of centrifugation of cylindrical samples at various revolution speeds, which comprises:
(1) centrifuging an assembly sample, saturated with a first fluid, constituted by the porous sample to be analysed (A), and a material (B) having the same permeability and approximately the same diameter as of (A), the material (B) being connected with the sample (A) through capillary contact along that section of (A) which is the farthest from the centrifuge rotor, with the ratio of the length of (A) to the length of (B) being comprised within the range of from 10:1 to 2:1, with the assembly constituted by (A) and (B) being immersed in a second fluid which is immiscible with the first fluid;
(2) measuring the saturation rate of the first fluid by weighing the only sample (A);
(3) correlating, for each measuring revolution speed, the so determined saturation rate value, with the corresponding average capillary pressure of (A)+(B) assembly.

2. Process according to claim 1, characterized in that the ratio of the length of (A) to the length of (B) is comprised within the range of from 7:1 to 4:1.

3. Process according to claim 1, characterized in that both the sample (A) and the material (B) are rock samples having the same lithological, permeability and porosity characteristics.

4. Process according to claim 3, characterized in that the material (B) comes from the same portion of well core as of (A).

5. Process according to claim 1, characterized in that the materials (A) and (B) are kept into capillary contact by means of a thin layer of cellulose soaked with the same fluid which initially saturated the sample.

6. Process according to claim characterized in that the capillary mutual contact of materials (A) and (B) is accomplished by simply putting (A) into contact with (B).

7. Process according to claim, 1, characterized in that the centrifugation is carried out at temperature comprised within the range of from 10 to 80° C.

* * * * *